US010369001B2

(12) United States Patent
VonGunten

(10) Patent No.: US 10,369,001 B2
(45) Date of Patent: *Aug. 6, 2019

(54) METHOD OF REPLACING THE NUCLEUS PULPOSUS OF AN INTERVERTEBRAL DISC

(71) Applicant: Eric R. VonGunten, Canton, OH (US)

(72) Inventor: Eric R. VonGunten, Canton, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/783,704

(22) Filed: Oct. 13, 2017

(65) Prior Publication Data

US 2018/0036135 A1 Feb. 8, 2018

Related U.S. Application Data

(60) Division of application No. 14/789,196, filed on Jul. 1, 2015, now Pat. No. 9,814,593, which is a continuation of application No. 13/780,921, filed on Feb. 28, 2013, now Pat. No. 9,095,443.

(60) Provisional application No. 61/644,063, filed on May 8, 2012.

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/441* (2013.01); *A61F 2/4611* (2013.01); *A61F 2002/30069* (2013.01); *A61F 2002/30583* (2013.01); *A61F 2002/30586* (2013.01); *A61F 2002/444* (2013.01); *A61F 2002/465* (2013.01)

(58) Field of Classification Search
CPC .. A61F 2/44; A61F 2/441; A61F 2/442; A61F 2002/444; A61F 2250/003; A61F 2310/00215; A61F 2210/0085

See application file for complete search history.

(56) References Cited

U.S. PATENT DOCUMENTS

| 2002/0147497 A1* | 10/2002 | Belef .................. A61F 2/02 623/17.12 |
| 2003/0195628 A1 | 10/2003 | Bao et al. |
| 2005/0154463 A1 | 7/2005 | Trieu |
| 2007/0073402 A1 | 3/2007 | Vresilovic et al. |

(Continued)

OTHER PUBLICATIONS www.campoly.com/documents/presentation/nucleus.pdf, Cambridge Polymer Group, Inc., An Injectable Hydrogel for Nucleus Pulposus Augmentation, 10 pages, Mar. 5, 2004.

(Continued)

*Primary Examiner* — Julianna N Harvey
(74) *Attorney, Agent, or Firm* — Sand, Sebolt & Wernow Co., LPA

(57) ABSTRACT

An implant configured to completely replace degenerated or damaged nucleus pulposus in an intervertebral disc. The implant comprises a silicone elastomer shell that is implanted into a void within the annulus fibrosus created by at least partial removal of the nucleus pulposus therefrom. A colloidal suspension of platinum cured silicone-based polymer and carbon nanotubes is injected into the elastomer shell. The colloidal suspension is irradiated with electromagnetic radiation, particularly infrared or near infrared light, to the point that it hardens. The hardened implant becomes a mechanical replacement for the original nucleus pulposus in the intervertebral disc.

20 Claims, 7 Drawing Sheets

(56) References Cited

U.S. PATENT DOCUMENTS

| | | |
|---|---|---|
| 2007/0173935 A1 | 7/2007 | O'Neil et al. |
| 2008/0009434 A1 | 1/2008 | Reches et al. |
| 2008/0154373 A1* | 6/2008 | Protopsaltis ....... A61B 17/7013 623/17.12 |
| 2009/0131939 A1* | 5/2009 | Ahrens ................ A61F 2/4405 606/80 |
| 2011/0125158 A1 | 5/2011 | Diwan et al. |
| 2011/0270391 A1 | 11/2011 | Chitre et al. |

OTHER PUBLICATIONS

Polymer Systems Technology Limited, A Guide to Silicone Dispersions, https://www.silicone-polymers.co.uk/pdfMaster/A%20guide%20to%20silicone%20dispersions.pdf, version uploaded Mar. 18, 2017, 12 pages.

* cited by examiner

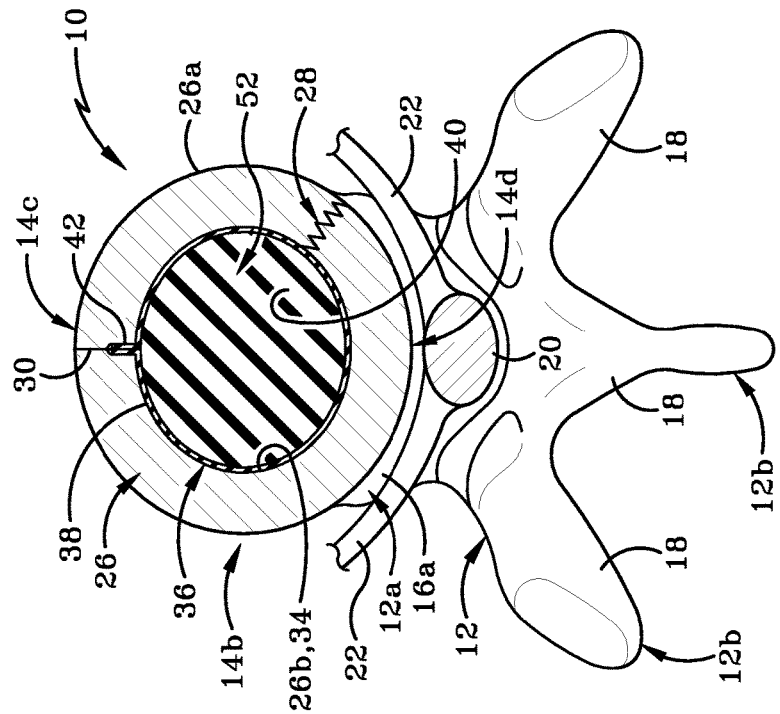
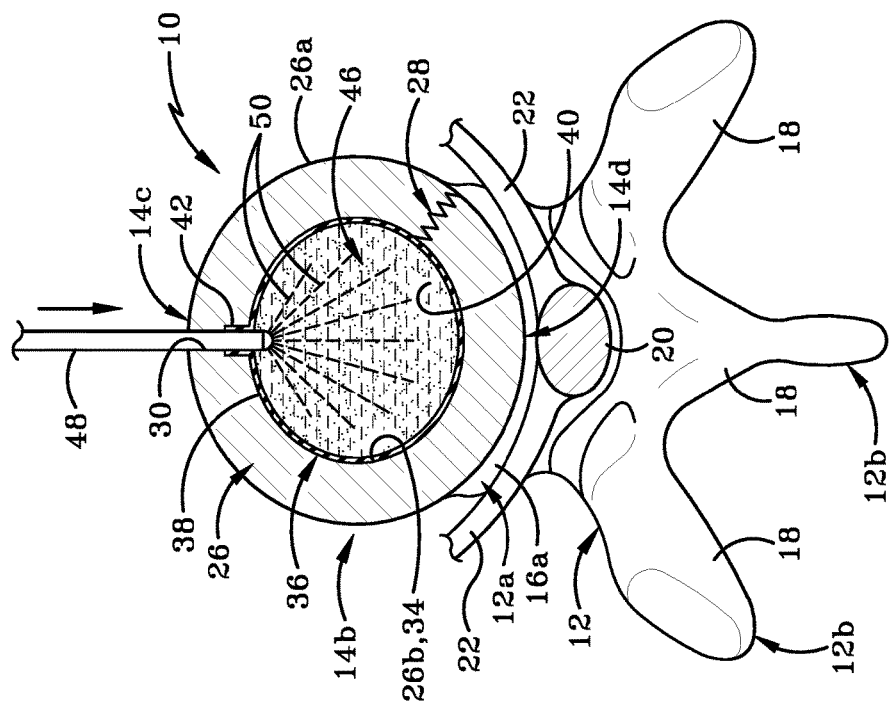
FIG-8
FIG-9

METHOD OF REPLACING THE NUCLEUS PULPOSUS OF AN INTERVERTEBRAL DISC

CROSS-REFERENCE TO RELATED APPLICATIONS

This application is a Divisional of U.S. patent application Ser. No. 14/789,196 filed Jul. 1, 2015, which is a Continuation of U.S. patent application Ser. No. 13/780,921 filed Feb. 28, 2013, now U.S. Pat. No. 9,095,443, which claims the benefit of U.S. Provisional Patent Application Ser. No. 61/644,063 filed May 8, 2012.

BACKGROUND OF THE INVENTION

Technical Field

This invention relates generally to treatments for back pain. More particularly, this invention relates to a treatment for degenerated, herniated or ruptured intervertebral discs. Specifically, this invention is directed to an apparatus and method for replacing the nucleus pulposus of a damaged intervertebral disc which includes removing the original nucleus pulposus, inserting an implant receptacle into the void in the disc created by the removal of the nucleus pulposus, injecting an implant substance into the implant receptacle, and applying electromagnetic radiation, particularly infra-red or near infra-red radiation, to the implant substance in the receptacle to harden it into a viscoelastic state so that it is able to perform in much the same manner as the original nucleus pulposus.

Background Information

The human spine is made up of a series of vertebrae that are separated from each other by intervertebral discs. The spine also includes other components such as ligaments, tendons, and the spinal cord. A network of nerves originates in the spinal cord and spreads outwardly into the body from the spine.

If one looks at the spine from the side, each intervertebral disc extends from the bottom of one vertebra to the top of the vertebra below it. The intervertebral discs are closed hydraulic systems that act as shock absorbers in the spine and they aid in absorbing the axial loads on the body. The discs act to bind the vertebrae together and also aid in helping the spine to twist and turn as the person moves.

Each intervertebral disc is made up two components, namely, the nucleus pulposus and the annulus fibrosus. The annulus fibrosus is a series of concentric lamellae or membranes formed from collagen in combination with proteoglycan and water. The lamellae are arranged in a special configuration to form a strong sac which surrounds and contains the nucleus pulposus. The annulus fibrosus is strengthened toward its posterior or back region by a ligament. A cartilaginous end plate is also a boundary for the top and bottom regions of the lamella and these plates contact the vertebrae above and below the intervertebral disc.

The nucleus pulposus is a semi-fluid, gelatinous substance which is essentially the material that absorbs shocks and allows the spine to pivot. The nucleus pulposus is under extremely high pressure and pushes outwardly on the lamellae and it is the job of the lamellae to contain this pressurized material.

As people age, the lamellae may become desiccated i.e., dehydrated, and degenerate to the point that they are no longer able to adequately contain the nucleus pulposus under pressure. A weakened area may develop in the annulus fibrosus and a small bulge or hernia can develop in this weakened area and extend outwardly beyond the outer perimeter of the annulus fibrosus. This bulge will tend to apply pressure to the nerves that are disposed adjacent the posterior region of the intervertebral disc, causing much pain and discomfort.

If the weakened area continues to deteriorate, the annulus fibrosus may rupture, spilling some of the nucleus pulposus material onto the surrounding nerves and tissues. This jelly-like substance contains chemicals that may cause inflammation and damage to the surrounding tissues and nerves and may therefore lead to an increase in pain. Additionally, with a ruptured disc, much of the shock absorbing property of the disc are lost, resulting in increased difficulty of movement for the patient and, again, a possible increase in the level of pain that they experience. The herniation or rupture of intervertebral discs is thought to be responsible for chronic back pain in around fifty percent of patients who suffer from back pain. It will be understood that traumatic injuries may also result in damage to intervertebral discs with the same consequences.

Another problem with aging is that the nucleus pulposus may itself become desiccated over time. As the nucleus pulposus shrinks, the intervertebral disc tends to collapse inwardly because there is no longer any outward pressure on the annulus fibrosus. As the disc collapses, the vertebrae may contact each other or may pinch nerves between them, thereby leading to much pain.

A number of solutions have been proposed in the art for treating patients with degenerated, ruptured, herniated or collapsing discs. In the case of ruptured or herniated discs, it has been proposed to make a small puncture in the annulus fibrosus to allow some of the nucleus pulposus to flow out of the disc. The puncture may be made in a variety of ways such as by way of a needle or a laser. Some have suggested that this type of treatment could suck the herniated portion of the nucleus pulposus back into the interior of the disc. Others have proposed partially or completely removing the nucleus pulposus from ruptured discs to reduce the pressure therein and to prevent leakage thereof into the surrounding nervous tissue. The removal or decrease in the quantity of nucleus pulposus within a disc has been accomplished through various means including application of heat, chemical treatments or treatment with radiofrequency energy, for example. Yet others have proposed entirely removing the intervertebral disc and then fusing the vertebrae together to prevent collapse of the spine. Such fusion may be accomplished by introducing a small piece of bone or titanium between those vertebrae which flank the removed disc. In other instances, parts of the adjacent vertebrae are surgically removed along with the disc and a bone graft and/or metal plate may be joined to those adjacent vertebrae to stabilize the spine. Still further, the intervertebral disc may be removed and an artificial disc may be surgically implanted into the spine. Finally, it has been proposed that the intervertebral disc be heated to a particular temperature (such as 90°) for a particular length of time (such as 15 minutes) in order to try and seal the ruptured lamellae.

While many of these procedures have helped patients, there is still a need in the art for a less invasive method of treating degenerated, herniated, ruptured or collapsed intervertebral discs that may restore much of the shock absorbing quality of the disc and may lead to a possible reduction in the levels of chronic back pain experienced by the patient.

BRIEF SUMMARY OF THE INVENTION

The device of the present invention is an improved spinal implant or prosthesis that is inserted into a void within the annulus fibrosus of an intervertebral disc created by the loss of nucleus pulposus therefrom. The implant comprises an implant receptacle in the form of a bag or shell which defines a cavity therein. An implant substance is injected into the implant receptacle's cavity and is then hardened. The implant receptacle is positioned within the void in the annulus fibrosus before the implant substance is introduced into the same.

The prosthetic disc of the present invention is designed to replace some or all of the degenerated or damaged nucleus pulposus within a void in the annulus fibrosus. In particular, the implant receptacle is a silicone elastomer bag that is implanted into the empty disc space and is then filled by introduction of an implant fluid into a cavity defined by the elastomer bag. More particularly, an implant fluid mixture is introduced into the bag's cavity. Still more particularly, the implant fluid mixture is a colloidal mixture. Preferably, the colloidal mixture is a colloidal suspension. Preferably the implant fluid is a platinum-cured silicone-based polymer which has carbon nanotubes mixed into the same. It will be understood, however, that a variety of other suitable implant fluids could be used instead of the platinum-cured silicone-based polymer with carbon nanotubes, without departing from the scope of the present invention. Most particularly, the implant substance selected is one that is capable of being changed from a fluid state to a substantially solid state in situ, i.e., within the void in the annulus fibrosus.

The disc void within the annulus fibrosus is an optimal prosthetic environment due to the lack of vascular tissue, i.e., blood vessels. Since the annulus fibrosus is naturally avascular, this reduces the likelihood of biological reaction, premature material breakdown, tissue interaction and/or rejection of the implant. The device of the present invention may be implanted into each of the levels of the spine containing a generally fully intact annulus fibrosus.

The method of the present invention is designed to improve the capabilities of spinal implants. Particularly, the method includes creating a hardened implant within the intact spinal disc space or annulus fibrosus. By leaving the overlying structures as intact as possible and hardening the implant within the body, it is expected that the life expectancy and viability of the implant will be improved over those known in the prior art. Since the present method targets only those discs that are degenerated or injured, the level of invasiveness of the surgery and the subsequent development of scar tissue within the body is kept to a minimum.

It is believed that the device and method of the present invention will prove to maximize retention of the patient's existing range of motion and will also improve or recapture any lost range of motion through proper rehabilitation of the patient.

Furthermore, by minimizing the structures being replaced within the spine, substantially all other avenues of addressing issues relating to the disc are still kept available to the surgeon and patient if the patient's health deteriorates further. Other treatment methods, including partial or complete disc replacement, for instance, are still available because the disclosed device and method does not cause damage to the annulus fibrosus or to the end plates.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

FIG. 8 is a cross-sectional view of the intervertebral disc showing the application of electromagnetic radiation of the implant fluid in the implant receptacle;

FIG. 9 is a cross-sectional view of the intervertebral disc showing the hardened implant fluid;

Similar numbers refer to similar parts throughout the drawings.

DETAILED DESCRIPTION OF THE INVENTION

Figure 1:
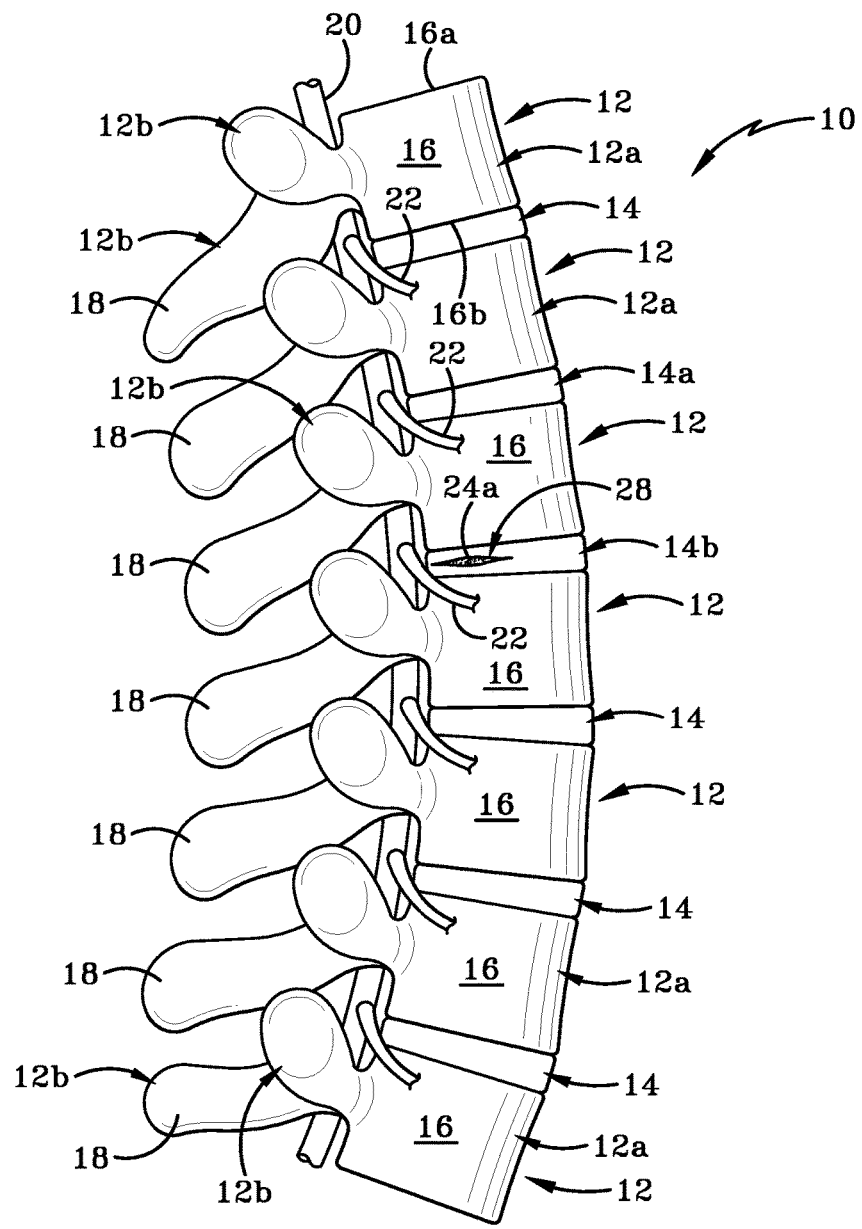
FIG. 1 is an illustrative side view of a portion of a spine showing the vertebrae and the intervertebral discs disposed therebetween.
Figure 2:
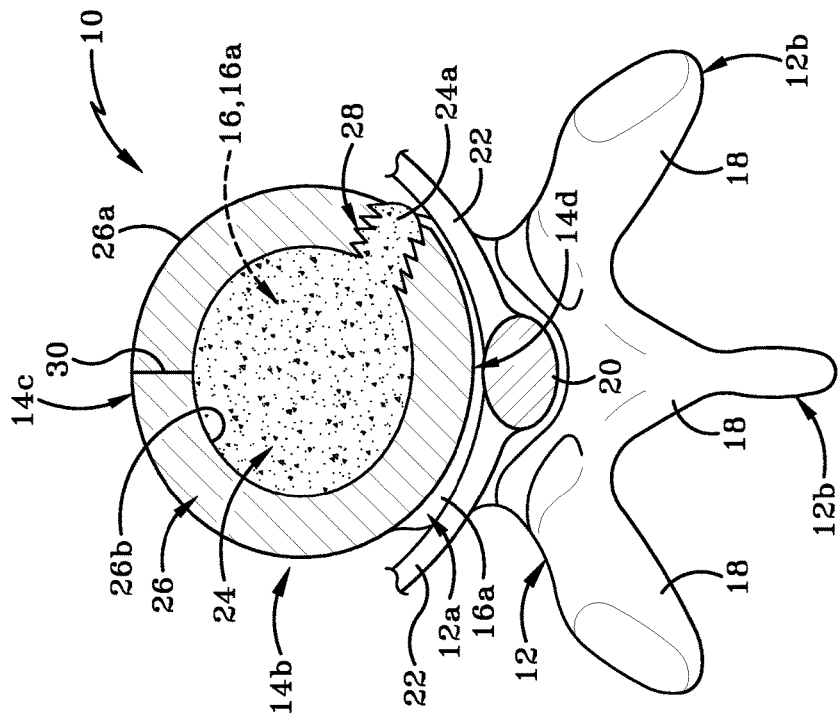
FIG. 2 is a cross-sectional view through line 2-2 of FIG. 1 showing a ruptured intervertebral disc.

Referring to FIGS. 1-2, there is shown a partial spine 10 of a patient in illustrative form only. The region of spine 10 depicted in FIG. 1 is a portion of the lumbar region of the spine. It will be understood, however, that the present invention is contemplated for use on any intervertebral disc in any part of the spine 10.

Spine 10 includes a plurality of vertebrae 12 and a plurality of intervertebral discs 14. Each vertebra 12 has an anterior region 12a and a posterior region 12b. The anterior region 12a is made up of a body 16 that is generally cylindrical in shape and has a generally flat upper surface 16a and a generally flat lower surface 16b. The posterior region 12b includes a plurality of processes 18 which extend rearwardly from the body. An aperture (not numbered) is defined between anterior and posterior regions 12a, 12b of vertebra 12 and the spinal cord 20 extends through this aperture. A plurality of nerves 22 radiate outwardly from spinal cord 20.

Each disc 14 extends between the lower surface 16b of a first vertebra 12 and the upper surface 16a of an adjacent second vertebra 12 disposed beneath the first vertebra in spine 10.

As shown in greater detail in FIG. 2, each intervertebral disc 14 is comprised of the nucleus pulposus 24 which is disposed within and surrounded by a plurality of fibrous membranes called the annulus fibrosus 26. In healthy discs, such as intervertebral disc 14a (FIG. 1), annulus fibrosus 26 is substantially continuous and entirely contains the nucleus pulposus 24 therein. In degenerated or injured discs, such as intervertebral disc 14b, a tear 28 may form in annulus fibrosus 26 and a quantity 24a of nucleus pulposus 24 flows through tear 28. The quantity 24a of nucleus pulposus 24 may contact a region of nerves 22 and inflame the same, causing pain. In other instances, not shown herein, a region of the annulus fibrosus 26 may weaken and a bulge may form in the annulus fibrosus being filled with a quantity of nucleus pulposus 24. This bulge will tend to project beyond the outer perimeter 26a of annulus fibrosus 26 and compress a region of nerve 22, causing pain.

Figure 3:
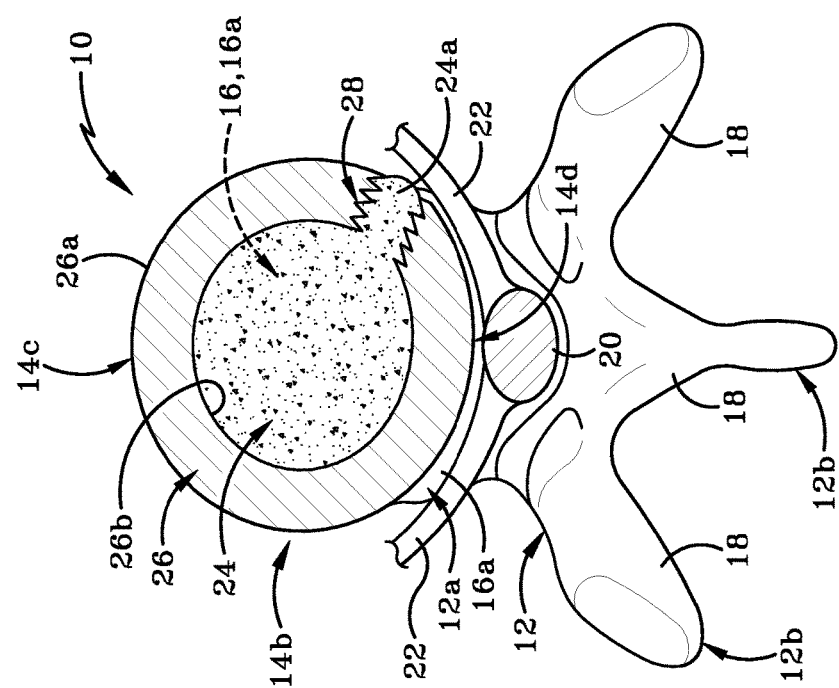
FIG. 3 is a cross-sectional view of the ruptured intervertebral disc of FIG. 2 showing a slit cut into an anterior portion thereof.

In accordance with a specific feature of the present invention, a method of treatment of this condition of a ruptured or herniated intervertebral disc 14b is disclosed. A first step in this method is shown in FIG. 3, where an incision is made in the anterior region 14c of intervertebral disc 14b. It will be noted that tear 28 has occurred in the posterior region 14d of intervertebral disc 14b. Bulges or ruptures in the discs 14 typically occur toward the posterior regions 14d thereof. The incision forms a slit 30 which extends from outer perimeter 26a of annulus fibrosus 26 through to the interior edge 26b thereof. Slit 30 may be oriented horizontally or vertically or at any angle in between. In particular, this slit 30 is small in size, typically from about ¼ inch in length to about 1 inch in length, and preferably is about ½ inch in length. Because of the diminutive size of slit 30, the annulus fibrosus 26 remains substantially intact and relatively undamaged by the procedure of the present invention. This is particularly important in cases where the nucleus pulposus 24 has been dehydrated or desiccated within the interior of the annulus fibrosus 26. Previously known procedures and devices have substantially damaged the annulus fibrosus during the attempt to insert a prosthetic disc into the spine. This damage increases the recovery time from the surgery and reduces the likelihood of success for the previously known procedures and devices.

Figure 4:
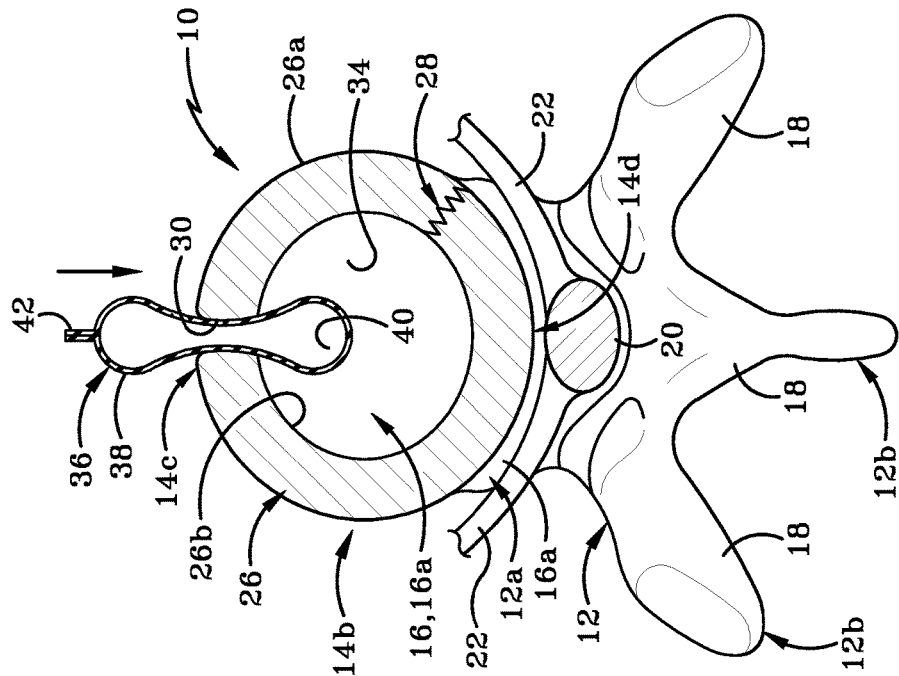
FIG. 4 is a cross-sectional view of the intervertebral disc of FIG. 2 showing the nucleus pulposus being removed therefrom.

The second step in the method in accordance with the present invention is shown in FIG. 4. In this second step, the nucleus pulposus 24 is removed from disc 14b. By way of example only, nucleus pulposus 24 is removed there from by suction but it will be understood that any other suitable methodology may be employed without departing from the scope of the present invention. As shown in FIG. 4, an evacuation tube 32 is inserted through slit 30 in the direction of arrow "A". Evacuation tube 32 preferably is connected to a vacuum source (not shown) and nucleus pulposus 24 is suctioned through tube 32 leaving a void 34 that is bounded and defined by annulus fibrosus 26. It will be noted that the region 24a of the nucleus pulposus 24 that extended through tear 28 may be at least partially suctioned back into the interior of disc 14b and be removed through tube 32. Any part of region 24a of the nucleus pulposus that remains outside of disc 14b is removed by the surgeon to prevent further damage to nerves 22 or any surrounding body tissue. The tissue damaged by tear 28 will collapse once the bulge or herniated region 24a is removed and over time will tend to knit together.

Figure 5:
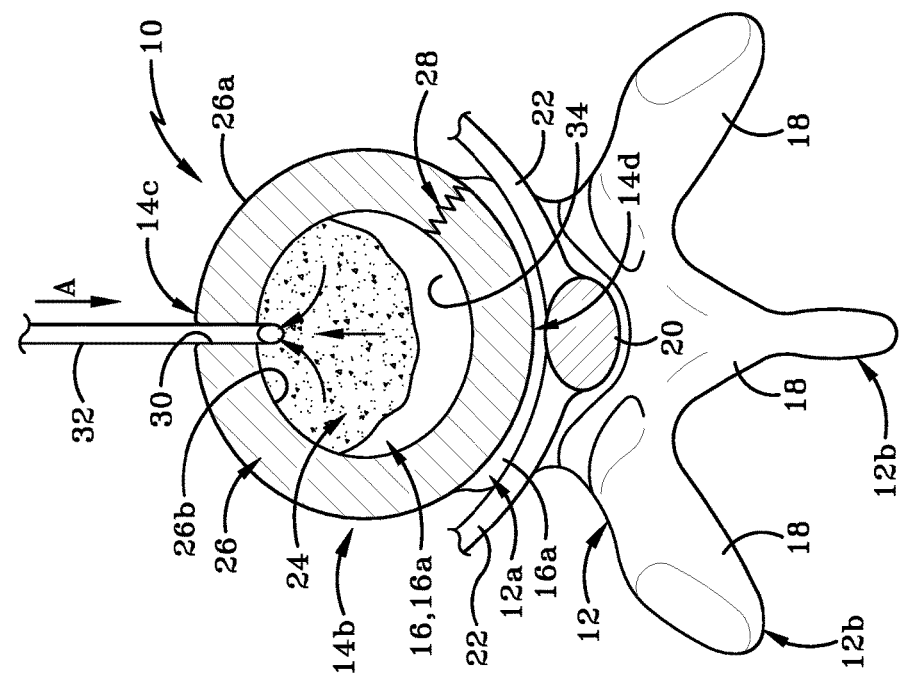
FIG. 5 is a cross-sectional view of the intervertebral disc of FIG. 4 showing the insertion of a first embodiment of an implant receptacle into the void created in the disc by removal of the nucleus pulposus.

FIG. 5 shows the next step in the method according to the present invention. In this step, an implant receptacle 36 in accordance with the present invention is introduced into void 34 through slit 30. Implant receptacle is a bag or sac having an outer wall 38 which bounds and defines an interior cavity 40. A one-way injection port 42 is provided in outer wall 38. In accordance with a specific feature of the present invention, outer wall 38 of implant 36 is comprised of a silicone elastomer. It will be understood that any other suitable material may be used for implant 36 without departing from the scope of the present invention.

Figure 6:
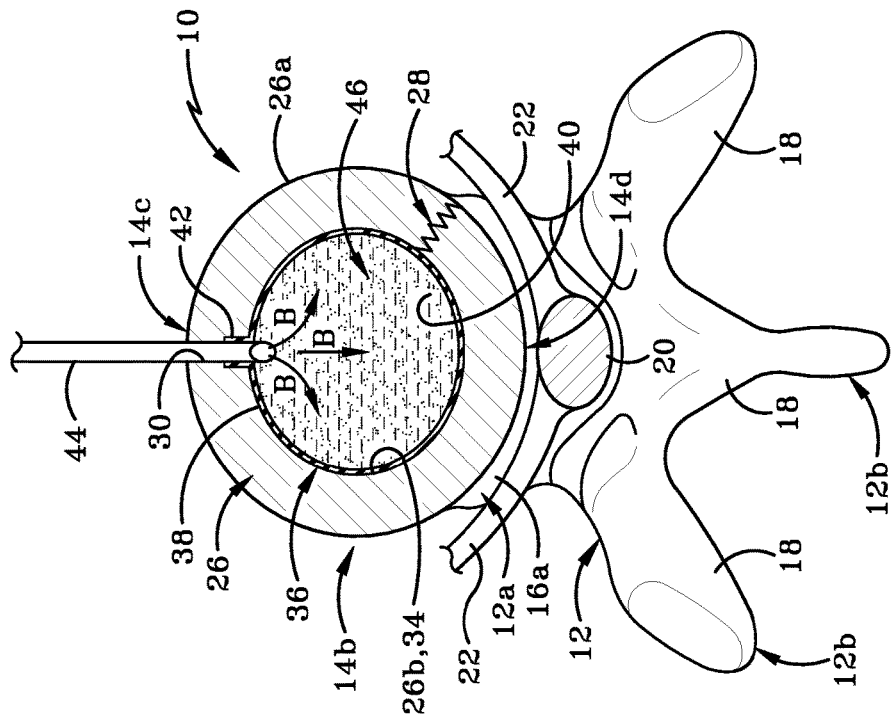
FIG. 6 is a cross-sectional view of the intervertebral disc of FIG. 5, showing the injection of implant fluid into the implant receptacle.
Figure 7:
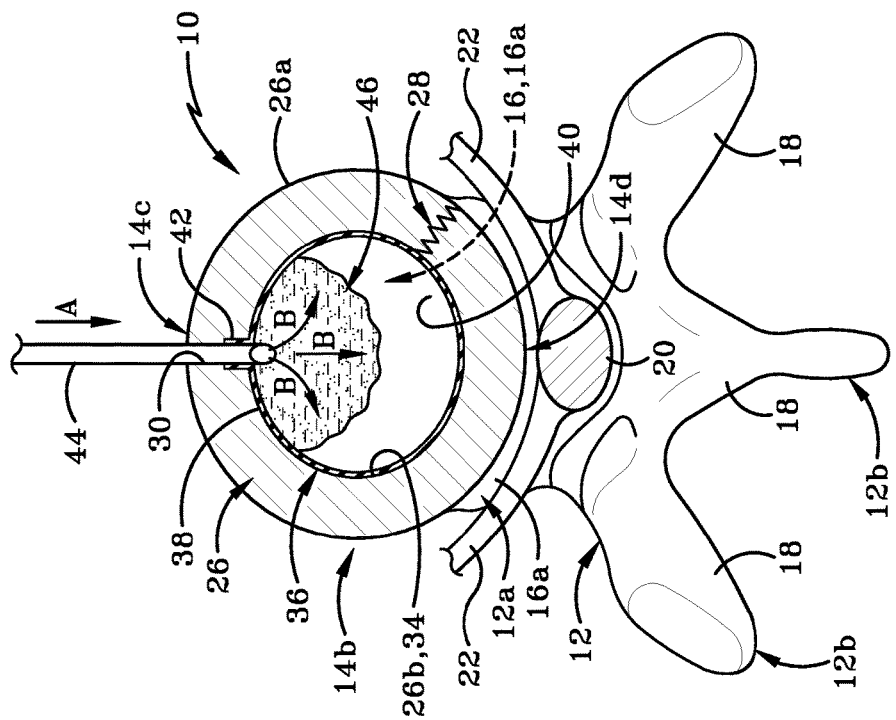
FIG. 7 is a cross-sectional view of the intervertebral disc showing the implant receptacle substantially filled with implant fluid.

FIG. 6 illustrates the next step in the method in accordance with the present invention. In this step, a needle 44 engaged with a syringe (not shown) is introduced through port 42 by moving it in the direction of arrow "A". An implant substance 46 is injected through needle 44 and port 42 into cavity 40 of implant receptacle 36. The arrows "B" show the flow of implant substance 46 into cavity 40. As implant substance 46 fills cavity 40, outer wall 38 of implant receptacle 36 abuts the inner surface 26b of annulus fibrosus 26 as shown in FIG. 7 and the void 34 that had previously been within disc 14b is filled with implant substance 46. As is evident from FIG. 7, outer wall 38 obstructs tear 28 and effectively seals a replacement nucleus pulposus within annulus fibrosus 26.

Implant substance 46 preferably is a polymer. The polymer selected for this procedure should ideally have two main characteristics. Firstly, the polymer preferably should be biologically inert in its components and secondly, the polymer should be able to be cured below 200° F., and ideally below 120° F. The biological inertness aids in ensuring that the implant does not include any harmful or damaging chemicals or reactants that could cause further injury to the patient. The curing temperature ensures that the process of hardening the implant does not heat the surrounding tissues, i.e., those of the annulus fibrosus, and any adjacent nerves and ligaments, to the point that they may become damaged by the heat.

It was found that a silicone based polymer is ideal for this purpose because of its range of durometer rating and its ability to be able to adjust the curing temperature to within the preferred biological implant range. Specifically, it has been found that a platinum cured silicone based polymer works well as an implant material.

In accordance with the specific feature of the present invention, implant substance 46 preferably is a colloidal suspension. In particular, implant substance 46 is a silicone-based polymer with carbon nanotubes suspended in the same. As indicated above, implant substance 46 preferably is a platinum-cured silicone-based polymer with carbon nanotubes suspended in the same. The carbon nanotubes are mixed into the polymer before injection to create the colloidal suspension that can then be injected as a single mixture.

It will be understood that other suitable implant substances may be introduced into implant receptacle 36 without departing from the scope of the present invention.

FIG. 8 illustrates the next step in the method in accordance with the present invention. In this step, a fiber-optic tube 48 is positioned to direct a beam 50 of electromagnetic radiation toward implant receptacle 36 and substance 46. In particular, the step involves directing a beam of infrared or near infrared radiation toward implant receptacle 36 and substance 46, i.e., directing a beam of electromagnetic radiation in the range of from about 700 nm to about 2500 nm toward receptacle 36 and substance 46. Specifically, it will be understood that for a platinum-cured silicone based polymer, the electromagnetic beam 50 is an infrared light beam having a wavelength of from about 700 nm to about 1000 nm. It will be understood, however, that the wavelength of electromagnetic radiation selected for use in the present invention will be dependent on the nature of substance 46 introduced into implant receptacle 36. The description of the present invention following hereafter will be directed toward the application of an infrared light beam 50 to substance 46.

Tube 48 or another delivery vehicle for the electromagnetic radiation may be positioned proximate receptacle 36 or may be introduced through port 42. Any suitable method of delivering the infrared light beam 50 to substance 46 may be utilized without departing from the scope of the present invention. Infrared light beam 50 is directed into implant substance 46 and is used to irradiate implant substance 46. The combination of polymer and carbon nanotubes is activated by the infrared light and is stimulated to harden. In particular, the infrared light beam 50 interacts with the carbon nanotubes in the suspension resulting in an exothermic reaction. In other words, heat is released into the implant substance 46 and this heat activates the polymer causing it to be internally heated to the appropriate temperature to begin hardening. The level of heating is sufficient to stimulate the curing process in the polymer but should not be high enough to damage surrounding tissue. Preferably, the temperature must be kept at a biologically safe range and ideally not go beyond 115° F. to 120°. In some instances and with the proper precautions, the temperature can be about 200° F. The temperature utilized depends on the location of the disc and the type of implant receptacle selected for implant. The target temperature will depend on the polymer mix selected for implant and the size of the implant. Once the curing reaction has been stimulated, the infrared laser may be stopped as the polymer mixture must only begin to harden to complete the implant process. If heat is an issue due to material selection or the location of the damaged disc on the spine, then the implant may be cured in steps over a number of days to minimize the risk of tissue damage.

It will be understood that both the polymer disclosed for use in the present invention and the temperature range at which that polymer is hardened are by way of example only. It will be understood that the same polymer disclosed herein may be hardened at temperatures higher than 200° F. if precautions are taken to protect the patient's tissues. Additionally, other polymers may be utilized for this procedure and those other polymers will be hardened at temperatures appropriate for the polymer selected.

Furthermore, the heating process of the selected polymers disclosed above tends not release any harmful or damaging chemicals or reactants, thus further minimizing the likelihood of tissue damage during the implant process. The polymer selected preferably also has minimal to no outgassing during the curing process. As will be disclosed later herein, the second and third embodiments of the implant receptacle in accordance with the present invention are designed to remove any gases that may be released during the cure process. The third embodiment also includes components that reduce the likelihood that heat generated by the curing process will damage the surrounding tissue.

Once implant substance 46 has been irradiated to the sufficient degree, tube 48 is withdrawn from port 42. Since port 42 includes a one-way valve, none of the substance 46 leaks out of implant receptacle 36. The slit 30 is then closed by any suitable means, such as by stitching. The hardened implant substance or the prosthetic nucleus pulposus that it has become is shown in FIG. 9 and is indicated by the reference character 52. The hardened implant substance 52 tends to exhibit the same properties as the original nucleus pulposus 24. Once in place and hardened, the implant in accordance with the present invention will be a complete mechanical replacement for the degenerated or injured intervertebral disc, allowing the patient to resume a near normal activity level after appropriate rehabilitation.

It will further be understood that it is not essential for the nucleus pulposus 24 to be removed from disc 14b during the procedure. If disc 14b has ruptured and a quantity of nucleus pulposus 24 has moved out of disc 14b through tear 28, it is contemplated that the void created in disc 14b by the partial loss of nucleus pulposus 24 can be filled by way of the steps following hereinafter.

Figure 11:
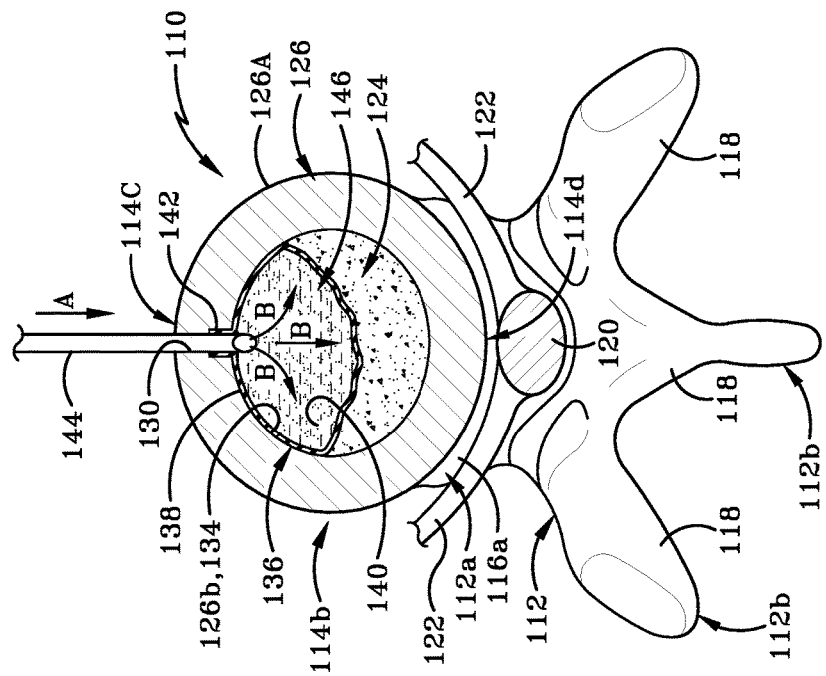
FIG. 11 is a cross-sectional view of the intervertebral disc of FIG. 10, showing the introduction of implant fluid into the implant receptacle so that the implant-fluid-filled implant receptacle occupies substantially the entire void within the annulus fibrosus.
Figure 10:
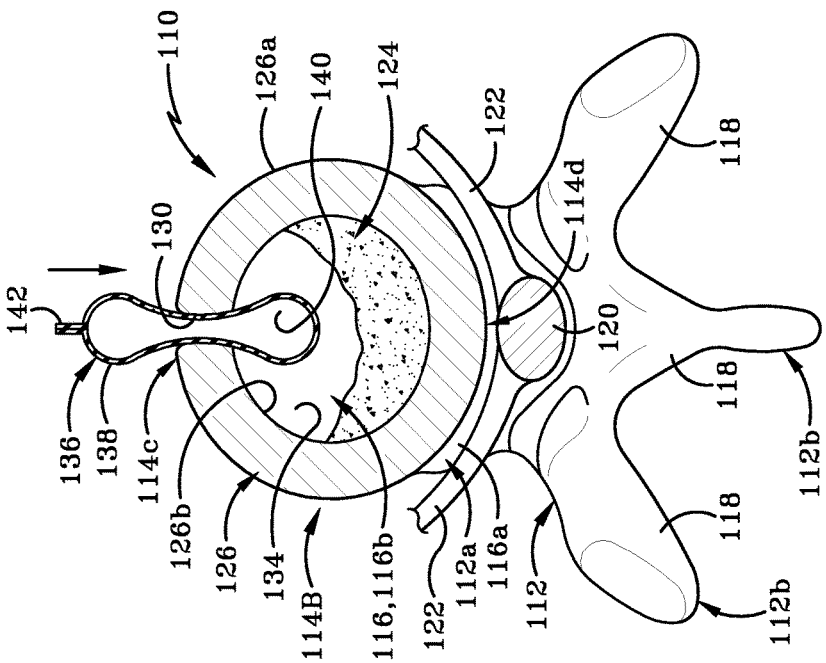
FIG. 10 is a cross-sectional view of an intervertebral disc showing the insertion of a first embodiment of an implant receptacle into the void created in the disc by desiccation of the nucleus pulposus.

In other instances, such as that illustrated in FIGS. 10 and 11, the nucleus pulposus 124 of intervertebral disc 114B in spine 110 has become desiccated or dehydrated. The quantity of nucleus pulposus 124 remaining in disc 114b is therefore inadequate to completely fill the space bounded by annulus fibrosus 126. Thus, a void 134 is created within annulus fibrosus 126. All other parts of spine 110 are substantially identical to spine 10. Spine 110 includes a plurality of vertebrae 112 and a plurality of intervertebral discs which include health discs (not shown) and damaged disc 114B. Each vertebra 112 has an anterior region 112a and a posterior region 112b. The anterior region 112a is made up of a body 116 that is generally cylindrical in shape and has a generally flat upper surface (not shown) and a generally flat lower surface 116b. The posterior region 112b includes a plurality of processes 118 which extend rearwardly from the body. An aperture (not numbered) is defined between anterior and posterior regions 112a, 112b and the spinal cord 120 extends through this aperture. A plurality of nerves 122 radiate outwardly from spinal cord 120.

If this situation with damaged disc 114B is left unaddressed, disc 114B will function less than optimally and could result in the patient experiencing loss of range of motion and a substantial amount of pain. Thus, in accordance with the present invention, an incision 130 is made in annulus fibrosus 126 and the slit so formed extends from the outer surface 126a of annulus fibrosus 126 to the inner surface 126b thereof. As with the previously described method, the incision or slit 130 is relatively small, being between ¼ inch and 1 inch in size, and preferably around ½ inch. (In particular, the incision 130 is far smaller than the dimensions of the hardened prosthetic disc that will remain within the void 134 after the procedure has been completed.) An implant receptacle 136 is inserted into void 134 within disc 114B. Implant receptacle 136 includes an outer wall 138 that bounds and defines an interior cavity 140. A one way valve 142 is provided on implant receptacle 136. It should be noted that implant receptacle 136 is substantially identical in structure and function to implant receptacle 36. It may be of a smaller size. The flexible receptacle 136 is inserted into void 134 and then a needle 144 or other delivery mechanism is inserted through valve 142 and a quantity of implant fluid 146 is inserted into cavity 140 of receptacle 136. It should be noted that the quantity of implant fluid 146 is sufficient to substantially expand and fill cavity to the point that substantially all of the void 134 is filled. Although not illustrated herein, it will be understood that all other previously described steps in the procedure will then be undertaken to change the state of implant fluid 146 from a liquid to a solid phase. After this phase change has occurred in situ within the annulus fibrosus, the implement which delivers the infrared light is withdrawn and the incision 130 is closed by any suitable method such as stitching. The implanted prosthetic nucleus pulposus formed by the hardened implant fluid 146, together with the remnant of the original nucleus pulposus 124 and the essentially undamaged annulus fibrosus 126, causes intervertebral disc 114B to function in much the same fashion as it would have before becoming damaged. Thus, the method disclosed herein is useful for augmenting the nucleus pulposus within a disc without requiring a tremendously invasive procedure. As with the previously described situation, substantially all currently known options for treating degenerating or damaged discs remain possible for use at a later time because of the fact that all of the other parts of the spine are essentially left intact and undamaged by the procedure disclosed herein.

Figure 12:
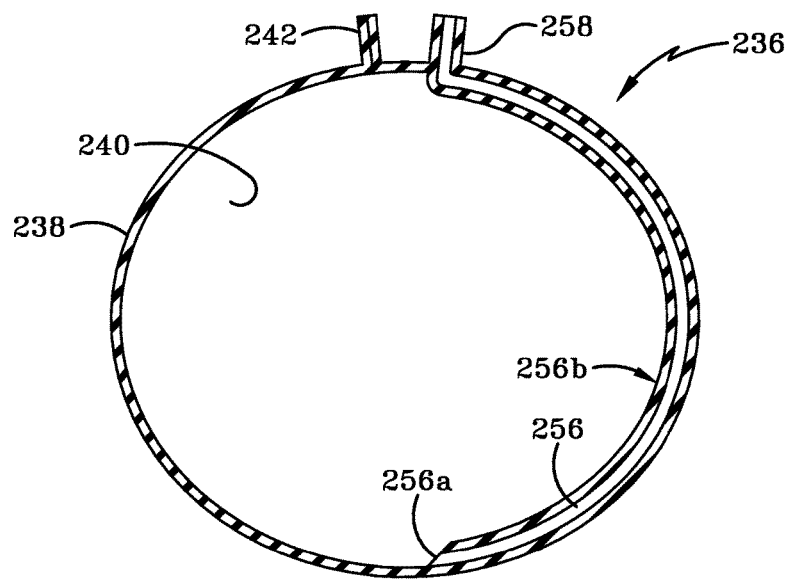
FIG. 12 is a cross-sectional view of a second embodiment of an implant receptacle in accordance with the present invention.

FIG. 12 shows a second embodiment of implant receptacle in accordance with the present invention and is generally indicated at 236. Implant receptacle 236 include an outer wall 238 which bounds and defines a cavity 240, and a one way port 242. Implant receptacle further includes an outgassing collection tube 256 which preferably is formed as part of outer wall 238. Collection tube 256 preferably includes a first region 256a comprising a semi-permeable membrane, and a second region 256b which may possibly be comprised of a semi-permeable membrane. Collection tube 256 terminates in an exhaust port 258. As the implant substance (not shown) is introduced into cavity 240, air in cavity 240 crosses over the semi-permeable membrane in first and second regions 256a, 256b. Additionally, the semi-permeable membrane allows gas that is produced during hardening of the implant substance to pass into collection tube 256 and be evacuated from implant receptacle 236 through exhaust port 258. Eventually, the hardening implant substance seals off the semi-permeable membrane.

Figure 13:
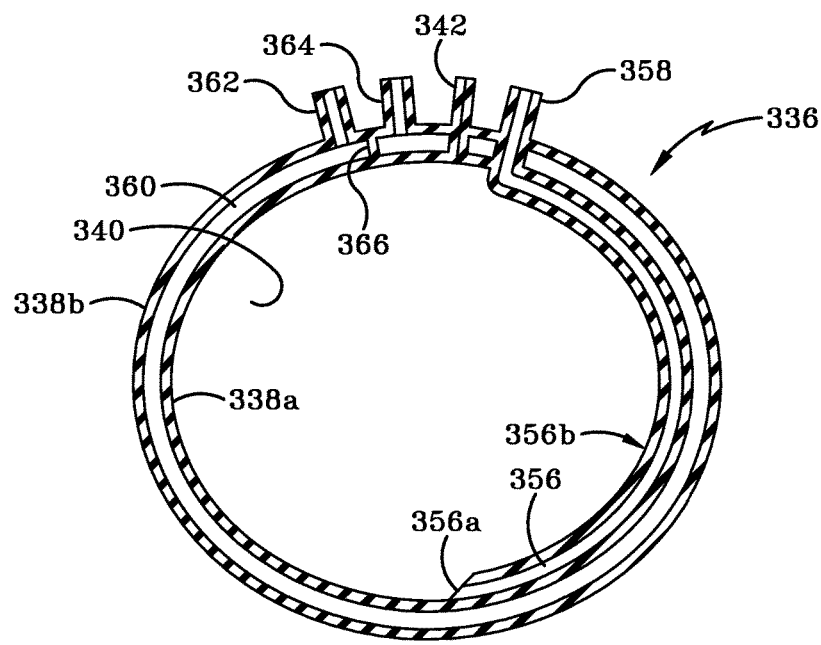
FIG. 13 is a cross-sectional view of a third embodiment of an implant receptacle in accordance with the present invention.

FIG. 13 shows a third embodiment of an implant receptacle in accordance with the present invention, generally indicated at 336. Implant receptacle 236 includes a first outer wall 338a and a second outer wall 338b. Both of the first and second outer walls 338a, 338b are made from a silicone elastomeric material. First outer wall 338a bounds and defines a cavity 340 into which the implant substance is introduced through a way-one-valved port 342. Implant receptacle 236 further includes a collection tube 356 having a first region 356a comprised of a semi-permeable membrane, and a second region 356b possible comprised of a semi-permeable membrane. As with the previous embodiment, collection tube 356 terminates in an exhaust port 358 and functions in the same manner as collection tube 256 and exhaust portion 258. In accordance with a specific feature of the present invention, second outer wall 338b is separated from first outer wall 338a by a gap 360. An intake port 362 and an outflow port 364 are provided in second outer wall 338b. A dividing wall 366 extends between first and second outer walls 338a, 338b and separates intake port 362 and outflow port 364. In accordance with the present invention a cooling fluid 268 is introduced into gap 360 to ensure that heat does not flow outwardly from implant substance to the annulus fibrosus 26.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A method of replacing at least part of the nucleus pulposus of an intervertebral disc in a patient's body, said method comprising the steps of:
   providing an implant substance, wherein the implant substance is a quantity of a colloidal suspension of a silicone-based polymer and a plurality of carbon nanotubes;
   inserting an implant receptacle into a void defined within the intervertebral disc;
   injecting the implant substance that is in a flowable state into a cavity defined by the implant receptacle;
   irradiating the implant substance with laser light from outside the patient's body; and
   changing the implant substance from a flowable state to a state that is similar to naturally-occurring nucleus pulposus.

2. The method as defined in claim 1, wherein the step of providing the quantity of the implant substance includes providing sufficient colloidal suspension to substantially occupy the entire void within the intervertebral disc.

3. The method as defined in claim 1, wherein the implant substance is irradiated until the implant substance is viscoelastic.

4. The method as defined in claim 1, wherein the step of irradiating the implant substance occurs within an annulus fibrosus of the patient's vertebra.

5. The method as defined in claim 1, wherein the step of injecting includes injecting the implant substance through a one-way valve or port located at an ingress into the implant receptacle.

6. The method as defined in claim 1, further comprising:
   removing a quantity of nucleus pulposus from the intervertebral disc to create the void into which the implant substance is injected.

7. A method of replacing at least part of the nucleus pulposus of an intervertebral disc in a patient's body, said method comprising the steps of:
   providing an implant substance;
   inserting an implant receptacle into a void defined within the intervertebral disc;
   injecting the implant substance that is in a flowable state into a cavity defined by the implant receptacle;
   irradiating the implant substance with laser light from outside the patient's body including:
      irradiating the implant substance with infrared to near infra-red laser light;
      energizing a plurality of carbon nanotubes located within the implant substance;
      releasing heat from the carbon nanotubes into the implant substance;
      hardening the implant substance; and
   changing the implant substance from a flowable state to a state that is similar to naturally-occurring nucleus pulposus.

8. The method as defined in claim 7, wherein the step of providing the quantity of the implant substance includes providing sufficient implant substance to substantially occupy the entire void within the intervertebral disc.

9. The method as defined in claim 7, wherein the implant substance is irradiated until the implant substance is viscoelastic.

10. The method as defined in claim 7, wherein the step of irradiating the implant substance occurs within an annulus fibrosus of the patient's vertebra.

11. The method as defined in claim 7, wherein the step of injecting includes injecting the implant substance through a one-way valve or port located at an ingress into the implant receptacle.

12. A method of forming an implant prosthesis for an intervertebral disc comprising the steps of:
- injecting a prosthetic material into a void defined by an annulus fibrosus of the intervertebral disc when the prosthetic material is in a fluid state, wherein the prosthetic material is a colloidal suspension of a silicone-based polymer and a plurality of carbon nanotubes;
- directing electromagnetic radiation in the form of infrared to near infrared laser light towards the prosthetic material when located within the void defined by the annulus fibrosus;
- energizing the plurality of carbon nanotubes within the prosthetic material;
- releasing heat from the plurality of carbon nanotubes into the prosthetic material; and
- altering the state of the prosthetic material, by way of the directed electromagnetic radiation, from a fluid state to a state where the altered prosthetic material is able to act as a shock absorber.

13. The method as defined in claim 12, wherein the directed electromagnetic radiation causes the generation of heat internally within the prosthetic material.

14. The method as defined in claim 13, wherein the step of generating heat includes generating heat that does not exceed a temperature which will damage surrounding body tissue.

15. The method as defined in claim 13, wherein the step of generating heat includes generating heat that does not exceed about 200° F.

16. The method as defined in claim 12 further comprising the step of making an incision in an annulus fibrosus of a patient's vertebra and injecting the prosthetic material into the void through the incision.

17. The method as defined in claim 16, further comprising stitching the incision closed after the step of altering the state of the prosthetic material.

18. The method as defined in claim 16, wherein the step of making the incision includes making the incision into an anterior region of the intervertebral disc.

19. The method as defined in claim 18, wherein the step of altering the prosthetic material occurs over more than one day.

20. The method as defined in claim 19, wherein the prosthetic material produces minimal to no out-gassing during the step of altering the state of the prosthetic material.

* * * * *